United States Patent

Mindermann

[11] Patent Number: 5,209,355
[45] Date of Patent: May 11, 1993

[54] METHOD AND AN APPARATUS FOR SORTING SOLIDS

[76] Inventor: Kurt-Henry Mindermann, Eggerscheidter Str. 112, D-4030 Ratingen 6, Fed. Rep. of Germany

[21] Appl. No.: 713,361

[22] Filed: Jun. 10, 1991

[30] Foreign Application Priority Data

Jun. 12, 1990 [DE] Fed. Rep. of Germany ....... 4018757
Jul. 11, 1990 [DE] Fed. Rep. of Germany ....... 4021882

[51] Int. Cl.⁵ .......................... B07C 5/34; G01N 3/06
[52] U.S. Cl. ...................................... 209/3.1; 209/11; 209/576; 209/930; 219/10.55 A; 219/10.55 M; 374/10; 374/122; 374/167
[58] Field of Search ................. 209/11, 576, 577, 908, 209/3.1, 3.2, 3, 930; 374/10-12, 122, 129, 167, 169; 219/10.55 R, 10.55 A, 10.55 M

[56] References Cited

U.S. PATENT DOCUMENTS

| | | | |
|---|---|---|---|
| 1,901,208 | 3/1933 | Vayda | 374/129 |
| 4,123,702 | 10/1978 | Kinanen et al. | 209/576 X |
| 4,212,397 | 7/1980 | Bockelmann | 209/576 X |
| 4,433,924 | 2/1984 | Quinn, III | 374/129 X |
| 4,933,075 | 6/1990 | Nordin et al. | 209/576 |

FOREIGN PATENT DOCUMENTS

| | | |
|---|---|---|
| 3113736A1 | 10/1982 | Fed. Rep. of Germany . |
| 3508253C2 | 9/1986 | Fed. Rep. of Germany . |
| 3834574A1 | 4/1990 | Fed. Rep. of Germany . |
| 566551 | 9/1974 | Switzerland ........................ 209/576 |
| 2076146 | 11/1981 | United Kingdom ................. 209/577 |
| 2125999 | 3/1984 | United Kingdom ................. 209/576 |
| 2188727 | 10/1987 | United Kingdom ................. 209/576 |

Primary Examiner—Donald T. Hajec
Attorney, Agent, or Firm—Frishauf, Holtz, Goodman & Woodward

[57] ABSTRACT

A method and an apparatus for sorting particulate solids material. The material is subjected to a microwave field and absorbs energy to an extent depending upon the dielectric properties of the individual particles. The absorbed energy heats the particles, and pyrodetectors detect the heat radiation. Detector output signals control pressurized air jets to remove particles from the waste material which are detected to be colder than the remainder of the bulk.

7 Claims, 1 Drawing Sheet

METHOD AND AN APPARATUS FOR SORTING SOLIDS

BACKGROUND OF THE INVENTION

The present invention relates generally to recycling methods and apparatus and, in particular, to a method and an apparatus for sorting particulate solid mixtures.

It would be easy to recycle waste if such waste would consist of only one material or one type of material, such as metals. Therefore, attempts are made to collect particular types of waste separately, such as glass, metal, paper, etc. However, most of the waste comprises a mixture of many different ingredients. Moreover, even if waste of a particular material is separately collected, one cannot be sure that in fact it will not contain others. For example, if glass bottles are collected, quite frequently one will also find metallic closure caps in the containers so that sorting of the waste is indispensable.

SUMMARY OF THE INVENTION

It is the primary object of the present invention to provide a method for sorting particulate mixtures of solids, and to provide an apparatus for implementing the method.

According to one aspect of the invention, a method is provided for sorting solids in response to their electric conductivity. The solids are subjected to a microwave field of predetermined power and frequency over a predetermined time interval. The power, frequency and duration are selected so as to have the solids assume different temperatures depending upon their dielectric properties. The temperature of the solids is detected, and the solids are sorted based on the detected temperatures.

According to another aspect of the invention, an apparatus is provided for sorting solids in response to their electric conductivity. The apparatus comprises a microwave furnace, means for conveying the solids through the furnace whereby the solids assume temperatures depending upon their dielectric properties, means for detecting the temperatures, and means for sorting the solids based on the detected temperatures.

The above-described method of the invention is based on the consideration that each substance has an electric conductivity or dielectric properties which are characteristic of the particular material. However, the electric resistance of an item does not only depend upon such conductivity but also upon the size and shape thereof, so that sorting based on direct measurement of the electric resistance of each particle seems impossible. The invention therefore provides that, firstly, the particles of the waste material are subjected to a microwave field where each particle absorbs energy in accordance with its dielectric properties, and the absorbed energy raises the temperature of the particles in accordance therewith. In a second step, the temperature of the particles is detected, preferably without physical contact, and the particles are sorted in response to their detected temperature.

German published patent application DE-31 13 736-A1 describes a method to locate reinforcement bars in concrete walls wherein the wall is subjected to a RF field so as to create inductive heating in the steel, and temperature differences are detected so as to identify the site where steel reinforcement bars may be found.

German published patent application DE-38 34 574-A1 discloses a method for microwave heating of different products contained in closed packings wherein the microwave power is varied in response to the temperature of each product when it enters a microwave chamber. Of course, in order to properly adjust the power, the material or at least its dielectric properties must be known beforehand.

BRIEF DESCRIPTION OF THE DRAWINGS

A preferred embodiment of an apparatus for implementing the method of the invention will be described in detail hereunder with reference to the attached drawings.

DETAILED DESCRIPTION OF THE INVENTION

An apparatus is provided to clean rotten or composted household and garden waste by ridding it of impurities such as glass, ceramic, plastics, metals and the like. It will be understood that other similar sorting processes may be implemented, e.g. the sorting of a mixture of plastic articles such as bottles or containers. It is known that the dielectric properties of materials, even if under normal conditions they are all considered to be "insulators" are quite different depending upon the composition of such material, and that those properties also vary somewhat with the, microwave frequency. Accordingly, depending upon the sorting criterion in terms of what is to be sorted from what, the microwave frequency, microwave power and the duration of the irradiation interval will be varied in order to heat materials which are to be separated from each other to different temperatures. Furthermore, it will be understood that sorting may be implemented in a plurality of cycles. For example, at first metals are separated from the remainder of the mixture by means of the method of the invention. Second, organic materials are separated from inorganic ones using again the method of the invention. In successive cycles, the microwave frequency and power as well as the irradiation interval will be adapted to suit the particular sorting criterion.

Figure 1:
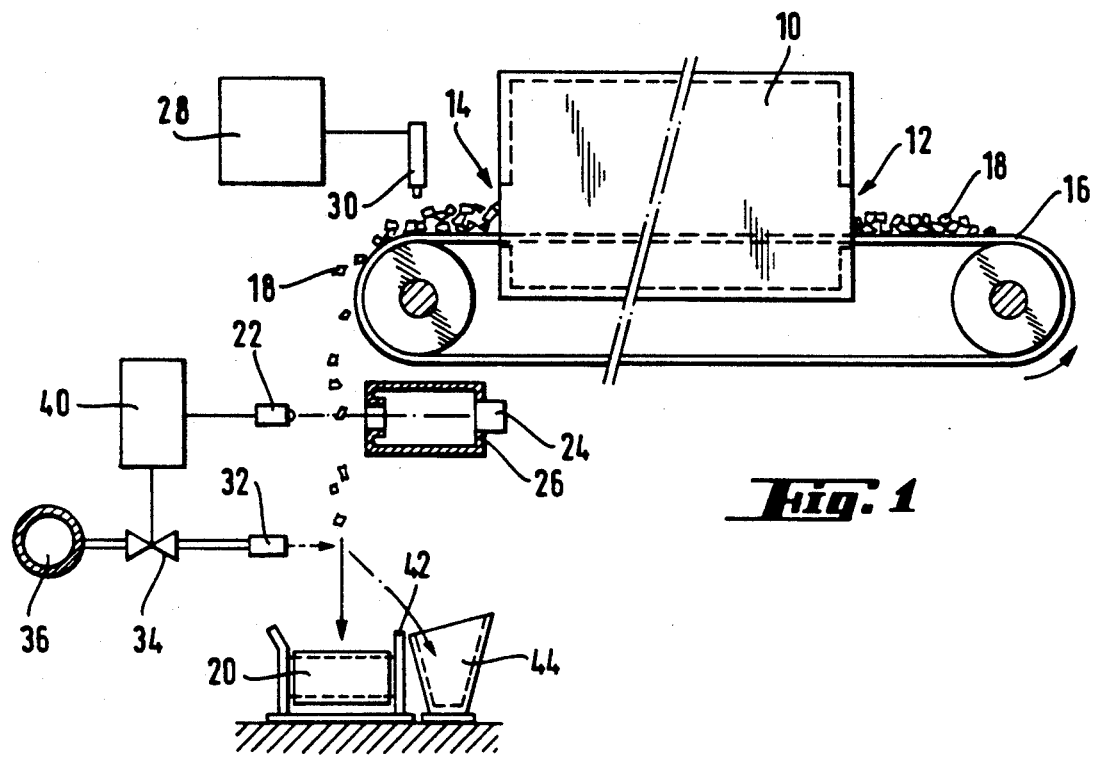
FIG. 1 illustrates the apparatus schematically in a side view.

As shown in FIG. 1, the apparatus comprises a microwave furnace 10 having an inlet 12 and an outlet 14. A belt conveyor 16 is loaded with to-be-cleaned compost 18 and conveys it through the furnace 10. Such furnaces including conveyor means are readily available.

The irradiated material passes through the furnace outlet 14 and falls freely unto a collector 20 which may also be a belt conveyor. Assuming that metals have been removed already in a first cycle, the compost has been heated in furnace 10 by the absorbed microwave energy while the "insulators" have absorbed very little energy and remain substantially at the temperature they had prior to their passage through the microwave field. However, due to heat conduction, those colder items may rapidly assume the temperature of their environment. Accordingly, the microwave power and the passage time are adjusted such that at the outlet 14, not much heat transfer has occurred.

Figure 2:
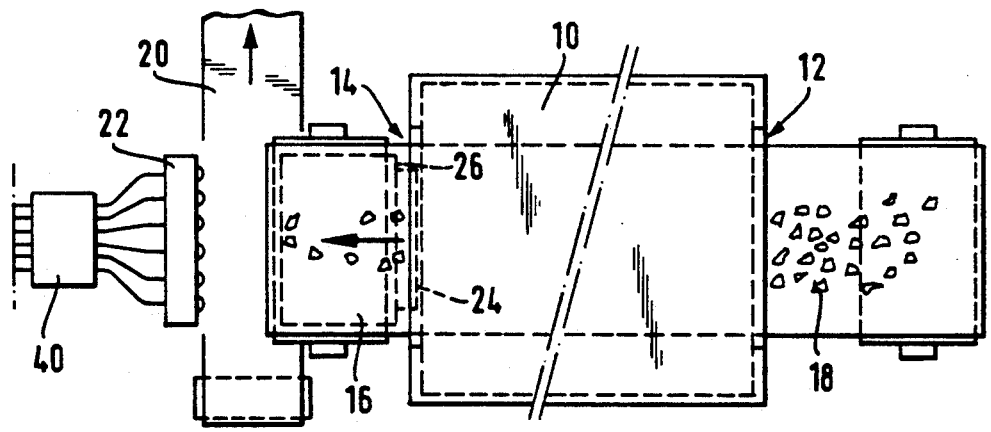
FIG. 2 is a partial top view of the apparatus.

As shown in FIG. 2, the falling material passes through a gap between a bank of pyrodetectors 22 and an artificial background opposite the pyrodetectors. This background consists of a radiating black body in the form of a box having an open front facing the pyrodetectors and heated to approach the temperature of the compost particles. For this purpose, a heater 24 is mounted on the exterior of the rear wall 26 of the box, and the heater is controlled by a control unit 28 in response to an input signal representative of the compost temperature measured by means of a thermometer 30.

The pyrodetectors therefore "see" a substantially constant temperature as long as there is no output from the microwave furnace or the output is only compost. However, if a relatively cold object falls across the detector bank, one or a plurality of the detectors will respond to the radiation transition attributable to such cold item. It has been found that a bank of detectors spaced about ten millimeter from one another is well suited to clean the compost sufficiently.

A detector particularly suited to detect heat radiation from a microwave-heated item is one which responds to radiation transitions. Such a detector is disclosed in German Patent Specification DE-35 08 253-B1. A transition from hot to cold (hot/cold) detected by pyrodetectors 22 produces a positive going spike, and a transition from cold to hot (cold/hot) produces a negative going spike.

Beneath the bank of detectors is a bank of nozzles 32, each nozzle being connected via a solenoid valve 34 to a manifold 36 supplied with pressurized air. Each individual solenoid valve 34 is controlled by the output signal of the particular pyrodetector 22 mounted above the nozzle 32 to which this solenoid valve is connected. A control unit 40 processes the output signals of pyrodetector 22 so as to amplify them and to delay them in accordance with the time a detected object will need to fall from the detector level to the nozzle level. Accordingly, the solenoid valves 34 are opened upon a hot/cold transition and closed upon a cold/hot transition. The air jet is directed such that a cold object is propelled beyond a partition wall 42 separating the compost collector 20 from a "non-compost" collector 44.

Control unit 40 can include an individual circuit for each combination of a detector 22 and its corresponding solenoid valve 34. Such a circuit would have an amplifier for amplifying the detector output to a level that can actuate a solenoid valve 34. The amplifier output signal is passed through a delay circuit which has been set to have a delay commensurate with the falling time between detector and nozzle. The output of the delay circuit could be inputted to a pulse forming circuit suitable for providing an actuating signal to the solenoid valve 34. An alternative version of control unit 40 has one such control unit for all of the detector/solenoid valve combinations. A multiplexing operation is utilized. Since such a technique and its associated circuitry are well known, further details are not deemed to be necessary.

It will be appreciated that various modifications of the preferred method as well as of the apparatus disclosed in detail above can be readily made. For example, if the compost is wetted before it is fed through the microwave furnace, the organic material will absorb much more energy than the inorganic so as to facilitate the sorting. Furthermore, instead of the belt conveyor which extends through the microwave furnace, the bulk of solids to be sorted could be fed to the furnace inlet and then made to fall therethrough freely. This may be suitable where different types of "insulators" are to be sorted. The air jet nozzles could be replaced with mechanical means. It is intended that all such modifications be included within the scope of the invention as defined by the following claims.

I claim:

1. An apparatus for sorting solid impurities out of a mixture of solids primarily constituted of particular solids, comprising:
   a microwave furnace having means to heat said mixture so that its constituents assume different temperatures depending upon their respective dielectric properties;
   means for conveying said mixture through said furnace;
   means for detecting said temperatures;
   a background radiation generator disposed opposite said detecting means, with said mixture falling between said detecting means and said generator, said background radiation generator includes means for producing a background radiation responsive to heat radiation of said mixture due primarily to said particular solids having a relatively high electric conductivity, and said detecting means distinguishing said solid impurities having a relatively low electric conductivity against said background radiation; and
   means for sorting said mixture of solids in response to the respective detected temperatures of the constituents thereof.

2. The apparatus of claim 1 wherein said conveying means include a belt conveyor.

3. The apparatus of claim 1 wherein said sorting means include controlled nozzles directing a jet of pressurized air against selected solid particles.

4. The apparatus of claim 1, wherein said detecting means comprises a bank of detectors and said sorting means comprises a bank of air jet nozzles respectively corresponding to said bank of detectors, and wherein said conveying means is adapted to drop heated solids so as to make them fall freely across said bank of detectors and thereafter across said bank of respectively corresponding air jet nozzles, and control means responsive to outputs of said detectors for switching said nozzles on and off based on respective outputs of said bank of detectors.

5. The apparatus of claim 1 wherein said detecting means include detectors responsive to temperature transitions.

6. The apparatus of claim 1 wherein said detector means include at least one detector responsive to heat radiation.

7. The apparatus of claim 6 wherein said detector is a pyrodetector.

* * * * *